United States Patent [19]
Cortekar et al.

[11] Patent Number: 6,146,619
[45] Date of Patent: Nov. 14, 2000

[54] PROCESS AND AGENTS FOR PERMANENTLY SHAPING KERATIN FIBRES

[75] Inventors: Hans-Wolfgang Cortekar, Remscheid; Doris Oberkobusch, Duesseldorf, both of Germany

[73] Assignee: Henkel Kommanditgesellschaft auf Aktien, Duesseldorf, Germany

[21] Appl. No.: 09/242,914

[22] PCT Filed: Aug. 25, 1997

[86] PCT No.: PCT/EP97/04622

§ 371 Date: Feb. 25, 1999

§ 102(e) Date: Feb. 25, 1999

[87] PCT Pub. No.: WO98/09606

PCT Pub. Date: Mar. 12, 1998

[30] Foreign Application Priority Data

Sep. 2, 1996 [DE] Germany ............... 196 35 481

[51] Int. Cl.[7] ................. A61K 7/06; A61K 7/09
[52] U.S. Cl. ............ 424/70.1; 424/70.2; 424/70.4; 424/70.51
[58] Field of Search ............. 424/70.1, 70.2, 424/70.5, 70.4, 70.51; 132/7

[56] References Cited

U.S. PATENT DOCUMENTS 3,910,289 10/1975 Wajaroff et al. ............... 137/7
4,834,971 5/1989 Klenk et al. ............... 424/70

FOREIGN PATENT DOCUMENTS

| 0 256 462 | 2/1988 | European Pat. Off. . |
| 0 713 695 | 5/1996 | European Pat. Off. . |
| 2 153 865 | 10/1985 | United Kingdom . |
| WO92/17155 | 10/1992 | WIPO . |
| WO96/09030 | 3/1996 | WIPO . |

OTHER PUBLICATIONS

D.H. Kirby in KPDR No. 1/2, p. 3–6 (1958).
Derwent Patent Abstract (WPAT) No. 88–050788/08.
Derwent Patent Abstract (WPAT) No. 92–332907/41.
Derwent Patent Abstract (WPAT) No. 96–188188/19.

*Primary Examiner*—Thurman K. Page
*Assistant Examiner*—S. Howard
*Attorney, Agent, or Firm*—Wayne C. Jaeschke; Glenn E. J. Murphy

[57] ABSTRACT

A process for permanently deforming keratin fibers is provided wherein the fiber is treated with 1) a keratin-reducing substance, 2) a physiologically compatible salt of an organic or inorganic acid anion and a divalent cation or $Al^{3+}$, and 3) a compound selected from the group consisting of Vitamin C, Vitamin $B_5$, derivatives thereof and mixtures thereof. The salt 2) and compound 3) can be applied in the form of a wave lotion or an intermediate treatment formulation. Also provided are wave lotions and hair treatment formulations comprising the salt 2) and the compound 3).

18 Claims, No Drawings

PROCESS AND AGENTS FOR PERMANENTLY SHAPING KERATIN FIBRES

BACKGROUND OF THE INVENTION

This invention relates to a process for the permanent deforming of keratin fibers, more particularly human hair, and to formulations suitable for use in this process.

The permanent deforming of keratin fibers is normally carried out by mechanically deforming the fibers and fixing the deformation by suitable auxiliaries. Before and/or after their deformation, the fibers are treated with an aqueous preparation of a keratin-reducing substance (wave lotion) and, after a contact time, are rinsed with water or with an aqueous solution. In a second step, the fibers are treated with an aqueous preparation of an oxidation agent (fixing lotion). After a certain contact time, the oxidizing agent is also rinsed out and the mechanical deforming aids (curlers, rollers) are removed from the fibers.

The wave lotion is normally alkalized so that the fiber swells and, as a result, the keratin-reducing substance is able to penetrate deeply into the fiber. The keratin-reducing substance splits some of the disulfide bonds of the keratin to —SH groups so that the peptide linkage is loosened and, through the stretching of the fibers by their mechanical deformation, the keratin structure is re-oriented. Under the influence of the oxidizing agent, disulfide bonds are re-established and, in this way, the deformation which the keratin structure has undergone is fixed.

A known process of the type in question is the permanent waving of human hair. This process may be applied both to produce curls and waves in straight hair and to straighten curly hair.

Although this process—known as permanent waving—is now widely used, it still cannot be considered to be optimal in regard to several parameters.

A crucial factor in achieving the required deformation is the so-called "strength" of the wave lotion which can be influenced through the quantity and type of reducing agent used and through the alkalinity of the wave lotion. However, wave lotions which guarantee satisfactory reshaping can cause damage to the point of breakage in the case of mismanaged hair and particularly in the case of oxidatively pretreated hair. In some cases, the scalp can also be adversely affected.

In addition, the usual acidification of the fixing lotion is not sufficient in most cases to return the hair to its original pH value within the contact time. The effect of this is that permanently waved hair is very susceptible, particularly to mechanical stressing, within the first few days of the treatment.

DESCRIPTION OF THE INVENTION

It has now surprisingly been found that the two above-mentioned drawbacks in particular can be remedied to a large extent by using a special combination of active substances. By adding this combination of active substances either to the wave lotion itself or to an additional intermediate rinse before fixing, the waving performance of the process can be increased to such an extent that either the alkalinity of the wave lotion can be reduced, milder reducing agents can be used and/or the reducing agent can be used in a smaller quantity. Conversely, it is possible by adding this combination of active substances to conventional wave lotions or intermediate rinses to obtain a stronger and longer-lasting wave effect.

Accordingly, the present invention relates to a process for the permanent deforming of keratin fibers, in which before and/or after mechanical deforming, the fibers are treated for a certain time with an aqueous preparation of a keratin-reducing substance (wave lotion), the wave lotion is optionally rinsed out, an intermediate treatment is optionally applied for a certain time, the intermediate treatment, if any, is rinsed out, the fibers are then fixed for a certain time with an aqueous preparation of an oxidizing agent (fixing lotion) and finally the fixing lotion is rinsed out with a rinse, characterized in that the wave lotion and/or the intermediate treatment contains a combination of active substances consisting of a physiologically compatible salt (A) consisting of the anion of an inorganic or organic acid and a divalent cation or $Al^{3+}$ and a vitamin or vitamin derivative (B) selected from vitamin C, vitamin $B_5$ and derivatives thereof.

The details of the teaching according to the invention are discussed in the following with reference to permanent wave formulations. However, the teaching may also be used with equal effect and with the same advantages for straightening naturally curled or chemically waved hair.

According to the invention, the active-substance combination mentioned above may be present in the wave lotion, in the intermediate treatment or in both.

In a first preferred embodiment of the process according to the invention, the active-substance combination is present only in the wave lotion. In this case, there is no need to apply an intermediate treatment or to rinse it out. The contact time of the wave lotion on the hair is as usual about 15 to 40 minutes.

In a second preferred embodiment of the process according to the invention, the active-substance combination is present only in an intermediate treatment. In this case, the contact time of the intermediate treatment is preferably between 2 and 15 minutes and more preferably between 5 and 10 minutes. Thereafter the intermediate treatment can be rinsed out, for example with clear water. However, it is preferred in this embodiment of the process according to the invention to leave the intermediate treatment on the hair and directly to apply the fixing lotion.

The present invention also relates to wave lotions and intermediate treatments containing the combination of active substances according to the invention.

The following observations on the active-substance combination according to the invention apply equally to its use in wave lotions and in intermediate treatments.

The first component of the active-substance combination according to the invention is a physiologically compatible salt (A) consisting of the anion of an inorganic or organic acid and a divalent cation or $Al^{3+}$.

The divalent cation of an alkaline earth metal or $zinc^{2+}$ is preferably used. The divalent cations of calcium, magnesium and zinc are particularly preferred, magnesium salts being most particularly preferred.

The inorganic acid which forms the anion of the salts (A) used in accordance with the invention is preferably selected from hydrohalic acids, sulfuric acid and phosphoric acid. The chlorides of the above-mentioned cations are particularly preferred.

A preferred organic acid which forms the anion of the salts (A) used in accordance with the invention is acetic acid.

Magnesium chloride and magnesium acetate represent particularly preferred salts (A) in the context of the present invention.

The second component of the active-substance combination according to the invention is a vitamin or vitamin derivative (B) selected from vitamin C, vitamin $B_5$ and derivatives thereof.

In a first preferred embodiment, ascorbic acid is used as component (B). Where ascorbic acid is selected as component (B), a stabilizer for ascorbic acid is preferably included in the formulation according to the invention. Ascorbic acid stabilizers are known to the expert and can be found in relevant publications. According to the invention, preferred stabilizers are complexing agents, such as EDTA, and thio compounds.

In another preferred embodiment, component (B) is selected from pantothenic acid, panthenol, panthenol esters and panthenol ethers. According to the invention, suitable panthenol esters and ethers are, for example, the triacetate of panthenol and panthenol monomethyl ester and its monoacetate. In this embodiment, it is particularly preferred to use panthenol.

Component (A) of the combination according to the invention is preferably present in quantities of 0.1 to 10% by weight, based on the particular formulation. Quantities of 0.2 to 5% by weight are preferred, quantities of 0.5 to 3% by weight being particularly preferred.

Component (B) of the combination according to the invention is preferably present in quantities of 0.1 to 10% by weight, based on the particular formulation. Quantities of 0.2 to 5% by weight are preferred, quantities of 0.2 to 2% by weight being particularly preferred.

Components (A) and (B) are preferably present in the combination according to the invention in a quantity ratio of 10:1 to 1:10 and, more preferably, in a quantity ratio of 1:2 to 1:4.

In addition, the formulations according to the invention preferably contain a dicarboxylic or tricarboxylic acid containing 2 to 6 carbon atoms and 0 to 2 hydroxy groups. Examples of such acids are oxalic acid, malonic acid, succinic acid, citric acid and tartaric acid. Of these acids, malonic acid is particularly preferred.

Where the formulations according to the invention are wave lotions, they contain the mercaptans known as keratin-reducing substances as a compulsory component. Examples of such compounds are thioglycolic acid, thiolactic acid, thiomalic acid, mercaptoethane sulfonic acid and salts and esters thereof, cysteamine, cysteine, Bunte salts and alkali metal salts of sulfurous acid. The alkali metal or ammonium salts or thioglycolic acid and/or thiolactic acid and also the free acids are particularly suitable. They are preferably used in the wave lotions in concentrations of 0.5 to 1.0 mole/kg for a pH value of 5 to 10 and, more particularly, 7 to 8.5.

The wave lotions according to the invention may additionally contain any of the usual ingredients of wave lotions, including for example:

Anionic surfactants such as, for example, soaps, alkyl sulfates and alkyl polyglycol ether sulfates, salts of ether carboxylic acids corresponding to the formula

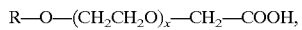

R—O—(CH$_2$CH$_2$O)$_x$—CH$_2$—COOH, in which R is a linear alkyl group containing 10 to 22 carbon atoms and x=0 or 1 to 16, acyl sarcosides, acyl taurides, acyl isethionates, sulfosuccinic acid mono- and dialkyl esters, linear alkane sulfonates, linear alpha-olefin sulfonates, alpha-sulfofatty acid methyl esters and esters of tartaric acid and citric acid with alcohols which are products of the addition of about 2 to 15 molecules of ethylene oxide and/or propylene oxide onto fatty alcohols containing 8 to 22 carbon atoms.

Zwitterionic surfactants such as, for example, betaines and 2-alkyl-3-carboxymethyl-3-hydroxyethyl imidazolines.

Ampholytic surfactants such as, for example, N-alkyl glycines, N-alkyl propionic acids, N-alkyl aminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids.

Nonionic surfactants such as, for example, products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group, $C_{12-22}$ fatty acid monoesters and diesters of addition products of 1 to 30 moles of ethylene oxide with glycerol, $C_{8-22}$ alkyl monoglycosides and oligoglycosides and ethoxylated analogs thereof and addition products of 5 to 60 moles of ethylene oxide with castor oil and hydrogenated castor oil.

Cationic surfactants, such as quaternary ammonium compounds containing 1–2 $C_{12-18}$ alkyl chains and 2–3 $C_{1-4}$ alkyl chains, pyridinium and imidazolinium salts, alkylamidoamines and so-called esterquats, such as the dialkyl ammonium methosulfates and methyl hydroxyalkyl dialkoyloxyalkyl ammonium methosulfates marketed under the trademark Steptanex®.

Protein hydrolyzates such as, for example, collagen hydrolyzates, elastin hydrolyzates, keratin hydrolyzates, hydrolyzates of wheat proteins, milk proteins, albumin proteins, silk proteins, almond proteins, soya protein and proteins from animal skins, collagen hydrolyzate condensates with organic acids such as, for example, oleic acid, myristic acid, undecylenic acid, cocofatty acid and abietic acid and salts thereof, elastin hydrolyzate condensates with fatty acids and cationic collagen hydrolyzates.

Thickeners, such as agar—agar, guar gum, alginates, xanthan gum and cellulose derivatives, such as hydroxyethyl and methylhydroxypropyl cellulose.

Structurants, such as glucose and maleic acid.

Cationic polymers, such as quaternized cellulose ethers, polysiloxanes containing quaternary groups, dimethyl diallyl ammonium chloride polymers, acrylamide dimethyl diallyl ammonium chloride copolymers, dimethyl aminoethyl methacrylate/vinyl pyrrolidone copolymers quaternized with diethyl sulfate, vinyl pyrrolidone/imidazolinium methochloride copolymers and quaternized polyvinyl alcohol.

Anionic, zwitterionic, amphoteric and nonionic polymers such as, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethyl ammonium chloride/acrylate copolymers, octyl acrylamide/methyl methacrylate/tert.butyl aminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Solubilizers, such as ethanol, isopropanol, glycerol and diethylene glycol.

pH regulators, such as sodium hydroxide, ammonia, ammonium carbonate, ammonium carbamate and citric acid/sodium citrate buffers.

Active substances, such as allantoin, pyrrolidone carboxylic acids and plant extracts.

Light stabilizers.

Complexing agents, such as NTA and phosphonic acids.

Swelling and penetration agents, such as glycerol, propylene glycol monoethyl ether, carbonates, hydrogen carbonates, guanidines,ureas and primary, secondary and tertiary phosphates.

Opacifiers, such as latex.

Dyes.

Perfume oils, dimethyl isosorbide and cyclodextrins.

Pearlescers, such as ethylene glycol monostearate and distearate and fatty alkanolamides.

Propellents, such as propane/butane mixtures, $N_2O$, dimethyl ether and air.

The contact time of the wave lotion on the hair is generally between 15 and 40 minutes, other influencing factors being the character of the hair, the chemical hair treatments already carried out, the required degree of deformation, the size of the mechanical deforming aids (hair curlers) used and the nature of the keratin-reducing agent.

The wave lotions according to the invention may be formulated as ready-to-use mixtures which may be directly applied either by the hairdresser or by the end user. However, it has proved to be of advantage or even necessary in some cases to formulate the wave lotions as so-called two-component mixtures which are first mixed by the user to form the ready-to-use wave lotion. In this case, one formulation contains the reducing agent in a suitable vehicle, for example water or an emulsion.

The intermediate treatments according to the invention may contain the same additional components as the wave lotions according to the invention. However, they will normally be free from reducing mercaptans or will only contain them in small amounts, for example to stabilize the ascorbic acid.

The process according to the invention is not limited in any way in regard to the use of known fixing lotions.

An essential ingredient of the fixing lotions are oxidizing agents, for example sodium bromate, potassium bromate, hydrogen peroxide, and the stabilizers normally used to stabilize aqueous hydrogen peroxide preparations. The pH value of such aqueous $H_2O_2$ preparations, which normally contain about 0.5 to 3.0% by weight of $H_2O_2$, is preferably in the range from 2 to 4 and is adjusted with inorganic acids, preferably phosphoric acid. Bromate-based fixing lotions contain the bromates in concentrations of, typically, 1 to 10% by weight, the pH of the solutions being adjusted to a value of 4 to 7. Fixing lotions based on enzymes (peroxidases) which contain small quantities, if any, of oxidizing agents, particularly $H_2O_2$, are also suitable.

The fixing lotions according to the invention are preferably formulated as solids. Accordingly, they contain the oxidizing agent in the form of a solid, for example potassium or sodium bromate. Water is only added just before use. In another possible and preferred embodiment, the oxidizing agent is formulated as a two-component system. The two components, of which one is preferably a hydrogen peroxide solution or an aqueous solution of another oxidizing agent while the other contains the remaining ingredients, are also mixed just before use.

In the process according to the invention, rinses are normally carried out with water to which inorganic salts may be added.

Both the wave lotion and the fixing lotion may be formulated as a creme, gel or liquid. The lotions may also be made up as foam aerosols which are packed in aerosol cans with a foam valve together with a liquefied gas such as, for example propane/butane mixtures, nitrogen, $CO_2$, air, $N_2O$, dimethyl ether, chlorofluorocarbon propellents or mixtures thereof.

EXAMPLES

General Procedure for Determining the Kirby Wave Value

To carry out the measurement, a 25 cm long smooth hair tress weighing 0.5 g, which had been tied in the same thickness at both ends, was moistened with the wave lotion. The hair tress was then placed firmly but without tension around the pins of the wave board, re-moistened with wave lotion and waved for 30 minutes at 37° C. The tress was rinsed on the board, immersed for 10 minutes in a fixing lotion at room temperature, rinsed, carefully removed from the wave board and then placed for 5 minutes in a water bath at 30° C. The linear distance between the 1st and 6th waves (5 waves)=$B_O$, =wave value was measured. Further particulars of the process can be found in the Article by D. H. Kirby in KPDR, No. 1/2, pages 3–6 (1958).

The following formulations were tested (all quantities in % by weight):

| Component | Wave lotion invention | Wave lotion comparison | Intermediate treatment invention |
|---|---|---|---|
| Thioglycolic acid | 8.0 | 8.0 | — |
| Eumulgin ® HRE 60[1] | 2.0 | 2.0 | — |
| Cremophor ® RH 40[2] | 2.0 | 2.0 | 2.0 |
| EDTA | 0.2 | 0.2 | 0.1 |
| Urea | 1.0 | 1.0 | — |
| Ammonium carbonate | 1.0 | 1.0 | — |
| Ascorbic acid | 2.0 | — | 2.0 |
| $MgCl_2$ | 1.0 | — | 1.0 |
| Perfume oil | 0.5 | 0.5 | 0.2 |
| Ammonia | to pH 8 | to pH 8 | — |
| Water | to 100 | to 100 | to 100 |

[1]Hydrogenated castor oil + 45 ethylene oxide (CTFA name: PEG-40-Hydrogenated-Castor-Oil) (BASF)
[2]Hydrogenated castor oil + 60 ethylene oxide (CTFA name: PEG-60-Hydrogenated-Castor-Oil) (HENKEL)

| Component | Fixing lotion |
|---|---|
| Hydrogen peroxide (50%) | 5.8 |
| EDTA | 0.2 |
| Dehyquart ® E[3] | 3.0 |
| Croquat ® WKP[4] | 0.5 |
| Perfume oil | 0.2 |
| Water | to 100 |

[3]N-(2-hydroxyhexadecyl-1)-N,N-dimethyl-N-2-hydroxyethyl ammonium chloride (28% active substance in water; CTFA name: Hydroxycetyl Hydroxyethyl Dimonium Chloride) (HENKEL)
[4]Cationic keratin hydrolyzate (CTFA name: Cocodimonium Hydroxypropyl Hydrolyzed Keratin) (CRODA)

The Kirby wave values obtained in the various tests are set out in the following Table:

| Formulation applied | Wave value [cm] |
| --- | --- |
| Wave lotion (invention) Intermediate rinse Fixing Rinse | 9.5 |
| Wave lotion (comparison) Intermediate rinse Fixing Rinse | 10.0 |
| Wave lotion (comparison) Intermediate rinse Intermediate treatment (invention) Fixing | 9.5 |

What is claimed is:

1. A process for permanently deforming keratin fibers, comprising:
   a. mechanically deforming a keratin fiber;
   b. treating the fiber with 1) a keratin-reducing substance, 2) a physiologically compatible salt of an organic or inorganic acid anion and a divalent cation or $Al^{3+}$, and 3) a compound selected from the group consisting of vitamin C, vitamin $B_5$, derivatives thereof, and mixtures thereof;
   c. fixing said treated and deformed fiber with an aqueous oxidizing agent; and
   d. rinsing the oxidizing agent from the fiber.

2. A process according to claim 1, wherein the salt b.2) and the compound b.3) comprise a wave lotion, which is applied to the fiber prior to fixing step c.

3. A process according to claim 2, wherein the wave lotion is rinsed from the fiber prior to fixing step c.

4. A process according to claim 1, wherein the salt b.2) and the compound b.3) comprise an intermediate treatment composition, which is applied prior to fixing step c.

5. A process according to claim 4, wherein the intermediate treatment composition is rinsed from the fiber prior to fixing step c.

6. A wave lotion comprising:
   a. a keratin-reducing mercaptan;
   b. a physiologically compatible salt of an organic or inorganic acid anion and a divalent cation or $Al^{3+}$; and
   c. a compound selected from the group consisting of Vitamin C, Vitamin $B_5$, derivatives thereof, and mixtures thereof.

7. A wave lotion according to claim 6, comprising 0.5 to 1.0 moles/kg of component a. and 0.1% to 10% by weight each of salt b. and compound c.

8. A wave lotion according to claim 7, comprising 0.2% to 5% by weight each of salt b. and compound c.

9. A wave lotion according to claim 8, comprising 0.2% to 2% by weight each of salt b. and compound c.

10. A wave lotion according to claim 7 having a pH of 5 to 10.

11. A wave lotion according to claim 8, having a pH of 7 to 8.5, wherein the weight ratio of salt b. to compound c. is 10:1 to 1:10.

12. A wave lotion according to claim 11, wherein the weight ratio of salt b. to compound c. is 1:2 to 1:4.

13. A wave lotion having a pH of 5 to 10 comprising:
    a. 0.5 to 1.0 moles/kg of a keratin-reducing mercaptan;
    b. 0.1% to 10% by weight of a physiologically compatible salt of an organic or inorganic acid anion and a divalent cation or $Al^{3+}$; and
    c. 0.1% to 10% by weight of a compound selected from the group consisting of Vitamin C, Vitamin $B_5$, derivatives thereof, and mixtures thereof.

14. A wave lotion according to claim 13, wherein the anion in salt b. is derived from an acid selected from the group consisting of hydrohalic acids, sulfuric acid, phosphoric acid, and acetic acid, the cation in salt b. is zinc or an alkaline earth metal cation, and compound c. is selected from the group consisting of ascorbic acid, pantothenic acid, panthenol, panthenol esters, and panthenol ethers.

15. A wave lotion according to claim 13, further comprising a $C_2$ to $C_6$ di- or tricarboxylic acid having 0 to 2 hydroxy groups.

16. A wave lotion according to claim 15, wherein the di- or tricarboxylic acid is oxalic acid, malonic acid, succinic acid, citric acid, or tartaric acid.

17. A hair treatment formulation comprising:
    a. 0.1% to 10% by weight of a physiologically compatible salt of an organic or inorganic acid anion and a divalent cation or $Al^{3+}$; and
    b. 0.1% to 10% by weight of a compound selected from the group consisting of Vitamin C, Vitamin $B_5$, and mixtures thereof.

18. A hair treatment formulation according to claim 17 comprising 0.2% to 5.0% by weight each of salt a. and compound b., wherein the anion in salt a. is derived from an acid selected from the group consisting of hydrohalic acids, sulfuric acid, phosphoric acid, and acetic acid, the cation in salt a. is zinc or an alkaline earth metal cation, and compound b. is selected from the group consisting of ascorbic acid, pantothenic acid, panthenol, panthenol esters, and panthenol ethers.

* * * * *